United States Patent
Cagle

(10) Patent No.: US 8,080,028 B2
(45) Date of Patent: Dec. 20, 2011

(54) SURGICAL DEVICE INCLUDES AN ANTI-MICROBIAL COATING

(75) Inventor: Gerald D. Cagle, Fort Worth, TX (US)

(73) Assignee: Novartis AG, Basel (CH)

( * ) Notice: Subject to any disclaimer, the term of this patent is extended or adjusted under 35 U.S.C. 154(b) by 1233 days.

(21) Appl. No.: 11/294,618

(22) Filed: Dec. 5, 2005

(65) Prior Publication Data

US 2007/0129743 A1 Jun. 7, 2007

(51) Int. Cl.
*A61B 17/32* (2006.01)

(52) U.S. Cl. .............. 606/167; 606/166; 30/142

(58) Field of Classification Search ............ 606/107, 606/133, 137, 166, 167, 174, 180, 184, 185, 606/186, 222, 223; 30/142, 147, 148, 149
See application file for complete search history.

(56) References Cited

U.S. PATENT DOCUMENTS

| 4,487,865 A | 12/1984 | Balazs et al. |
| 4,500,676 A | 2/1985 | Balazs et al. |
| 4,663,233 A | 5/1987 | Beavers |
| 4,801,475 A | 1/1989 | Halpern et al. |
| 5,023,114 A | 6/1991 | Halpern et al. |
| 5,037,677 A | 8/1991 | Halpern et al. |
| 5,149,543 A * | 9/1992 | Cohen et al. ................ 424/499 |
| 5,258,002 A | 11/1993 | Jeffers et al. |
| 5,266,359 A * | 11/1993 | Spielvogel ............... 427/388.4 |
| 5,649,922 A | 7/1997 | Yavitz |
| 5,702,717 A * | 12/1997 | Cha et al. ..................... 424/425 |
| 5,713,915 A | 2/1998 | Van Heugten et al. |
| 5,728,117 A | 3/1998 | Lash |
| 6,238,799 B1 * | 5/2001 | Opolski .................... 428/423.1 |
| 2003/0203991 A1 * | 10/2003 | Schottman et al. ........... 523/334 |
| 2004/0116792 A1 * | 6/2004 | Nesbitt ......................... 600/373 |
| 2006/0217750 A1 | 9/2006 | Ghannoum |

* cited by examiner

*Primary Examiner* — Tuan Nguyen

(57) ABSTRACT

A surgical knife blade or other surgical device containing an anti-microbial coating. The coating may be adhered to the device by a water-soluble adhesive that allows the anti-microbial coating to be released into the wound track. The coating may be of a consistency that allows a certain amount of the coating to slough off and pool or puddle around the surgical site as the surgical device is moved into and out of the surgical site.

9 Claims, 2 Drawing Sheets

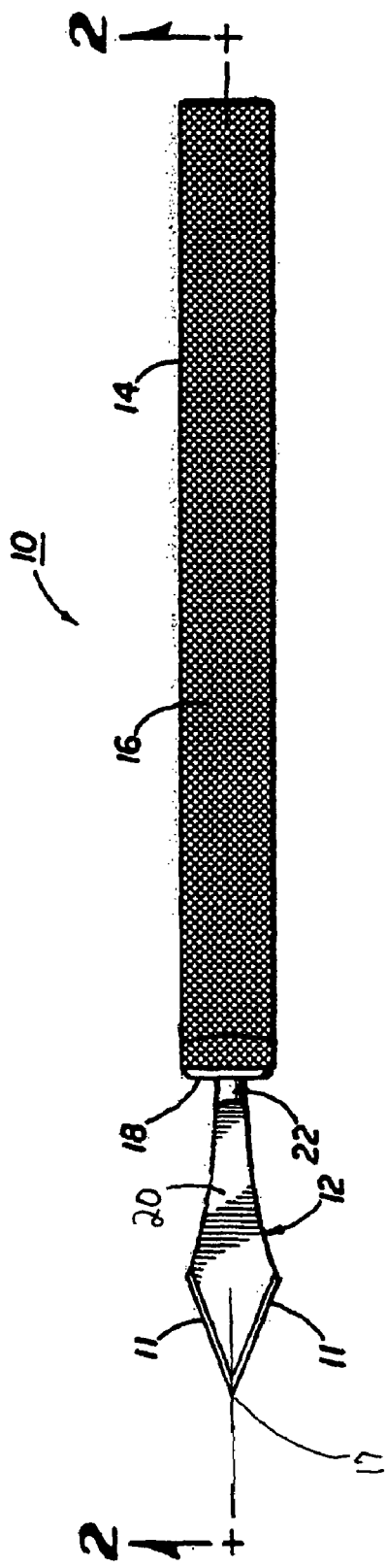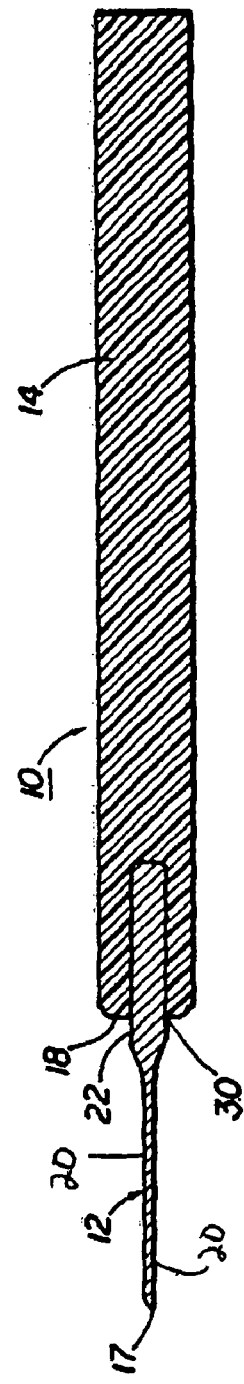

SURGICAL DEVICE INCLUDES AN ANTI-MICROBIAL COATING

BACKGROUND OF THE INVENTION

This invention relates generally to surgical knives and other surgical devices and particularly to knives used in ophthalmic surgery.

For many years, the predominant method of treating a diseased lens has been to remove the diseased lens and replace it with an intraocular lens ("IOL"). Two surgical procedures are preferred for removing the diseased lens: extracapsular cataract extraction and phacoemulsification. Extracapsular cataract extraction involves removing the lens in a relatively intact condition by use of a vectus or similar surgical instrument. Phacoemulsification involves contacting the lens with the vibrating cutting tip of an ultrasonically driven surgical handpiece to emulsify the lens, thereby allowing the emulsified lens to be aspirated from the eye. Although extracapsular cataract extraction has been the preferred surgical technique, phacoemulsification has become increasingly popular, in part because the cutting tip of the ultrasonic handpiece requires only a relatively small (approximately 3 to 3.5 millimeter) tunnel incision.

A typical posterior chamber IOL comprises an artificial lens ("optic") and at least one support member ("haptic") for positioning the IOL within the capsular bag. The optic may be formed from any of a number of different materials, including polymethylmethacrylate (PMMA), polycarbonate, silicon and soft acrylics, and it may be hard, relatively flexible or even fully deformable so that the IOL can be rolled or folded prior to insertion. The haptics generally are made from some resilient material, such as polypropylene, PMMA or soft acrylic. IOL's may be characterized as either "one-piece" or "multi-piece." With one-piece IOL's, the haptic and the optic are formed integrally as a blank and the IOL is then milled or lathed to the desired shape and configuration. Multi-piece IOL's are formed either by attaching the haptic to a preformed optic or by molding the optic around the proximal end of the haptic.

Endophthalmitis has always been a concern during ophthalmic surgery, and ophthalmic surgical procedures generally include the application of an intra-operative and/or post-operative antimicrobial agent; however, endophthalmitis can still occulr in a small percentage of cases.

Therefore, a need continues to exist for a device to help reduce the risk of endophthalmitis following ophthalmic surgery.

BRIEF SUMMARY OF THE INVENTION

The present invention improves upon the prior art by providing a surgical knife blade or other surgical device containing an anti-microbial coating. The coating may be adhered to the device by a water-soluble adhesive that allows the anti-microbial coating to be released into the wound track. The coating may be of a consistency that allows a certain amount of the coating to slough off and pool or puddle around the surgical site as the surgical device is moved into and out of the surgical site.

Accordingly, one objective of the present invention is to provide an anti-microbial surgical knife.

Another objective of the present invention is to provide a surgical knife containing an anti-microbial coating.

Another objective of the present invention is to provide a surgical knife that helps reduce the risk of endophthalmitis.

Another objective of the present invention is to provide a reservoir of material around the incision site to provide anti-microbial activity during the duration of the surgical procedure and during the exchange of instruments into and out of the surgical site.

These and other advantages and objectives of the present invention will become apparent from the detailed description and claims that follow.

BRIEF DESCRIPTION OF THE DRAWINGS

FIG. 1 is a plan view of the surgical knife containing the coating of the present invention.

FIG. 2 is a cross-sectional view of the knife illustrated in FIG. 1 taken along line 2-2.

DETAILED DESCRIPTION OF THE PREFERRED EMBODIMENTS

Figure 3:
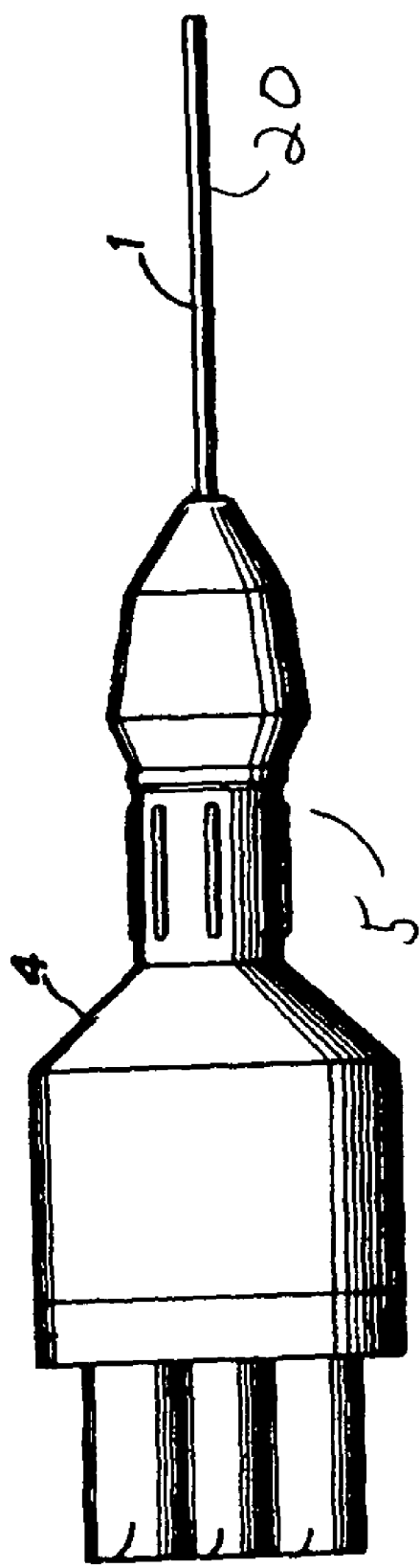
FIG. 3 is a plan view of an alternative surgical device containing the coating of the present invention.

As can be seen in FIGS. 1 and 2, surgical knife 10 of the present invention includes a blade 12 and a handle 14. Knife 10 may be either reusable or disposable. If knife 10 is reusable, blade 12 may be made of any suitable material such as stainless steel or titanium and handle 14 may be made from stainless steel, titanium, or aluminum. If knife 10 is disposable, handle 14 also may be made of suitable thermoplastic, fiberglass or composite material. Handle 14 is preferably cylindrical, although other cross-sectional shapes may also be used, and may contain knurling or other suitable roughening 16 to make handle 14 more positive to grip.

As can be seen in FIG. 2, blade 12 preferably has a thin cross-section (approximately 0.5 mm) and may be formed either from a sheet material or by flattening the end of round wire 22 with an approximate diameter of 1.5 mm. Blade 12 may be straight, as shown in FIG. 2, or angled relative to handle 14. Blade 12 is attached to end 18 of handle 14 by any conventional means such as integrally molding blade 12 within handle 14 or a collet (not shown). Tip 17 is preferably between 1.0 mm and 2.5 mm wide so as to fit easily through the typical incision used for the phacoemulsification cutting tip. Cutting edges 11 are preferable ground at an angle of approximately between 25° and 55° relative to the plane in which blade 12 lays. Blade 12 preferably has is coated with an anti-microbial agent 20, such as betadine (povidone-iodine). Agent 20 can either be water-soluble, so that contact with the incision dissolves agent 20 and agent 20 remains within the wound track following completion of the surgical procedure, or agent 20 can be temperature sensitive so that warming of agent 20 within the incision cause agent 20 to melt. Alternatively, agent 20 can be bound to blade 12 by a viscoelastic substance, such as hyaluronic acid, as described in U.S. Pat. Nos. 4,487,865, 4,500,676, 4,663,233, 4,801,475, 5,023,114 and 5,037,677, or by a hydrophilic coating comprising a polyurethane polymer matrix, such coatings being described in U.S. Pat. No. 6,238,799. Preferably, the substance used to bind agent 20 to blade 12 will also enter the wound track along with agent 20 and act as a sealant or adhesive within the wound track. Agent 20 may also be applied to blade 12 so that some of agent 20 sloughs off of blade 20 and pools or puddles around the wound site, thereby providing a reservoir of agent 20 that blade 12 passes into and out of the wound.

Although the description above was directed to surgical knives, one skilled in the art will recognize that other surgical devices, such as surgical device 5 having shaft 1 attached to body 4 shown in FIG. 3, may contain agent 20 on shaft 1.

Agent 20 may be applied to shaft 1 in the manner described above so that some of agent 20 sloughs off of shaft 1 and pools or puddles around the wound site, thereby providing a reservoir of agent 20 that recoats shaft 1 as probe 5 is manipulated within the wound.

This description is given for purposes of illustration and explanation. It will be apparent to those skilled in the relevant art that changes and modifications may be made to the invention described above without departing from its scope or spirit.

I claim:

1. A surgical knife, comprising:
 a handle and a blade attached to the handle, the blade being coated with an anti-microbial coating;
 wherein at least a portion of the coating on the blade is adhered to the blade with a water soluble adhesive and a consistency of the at least a portion of the coating is controlled to cause the at least a portion of the coating to slough off of the blade to pool or puddle around a wound site to provide a reservoir of the coating for the blade to pass back and forth through as the blade passes into and out of the wound site;
 wherein the coating further comprises a binding substance that is configured to act as a sealant or adhesive within the wound site; and
 wherein the surgical knife is a first surgical instrument and wherein the reservoir created by the pooled coating is configured to coat a second surgical instrument inserted into the wound site after the knife is removed.

2. The surgical knife of claim 1 wherein the anti-microbial coating is povidone-iodine.

3. The surgical knife of claim 1, wherein an amount of the coating configured to slough off is set by controlling a consistency of the coating.

4. A surgical device, comprising:
 a body and a shaft attached to the body, the shaft being coated with an anti-microbial coating;
 wherein at least a portion of the coating on the shaft is temperature sensitive to melt when the coating is warmed within a wound site to cause the at least a portion of the coating to slough off of the shaft to pool or puddle around the wound site to provide a reservoir of the coating for the shaft to pass back and forth through as the shaft passes into and out of the wound site;
 wherein the surgical device is a first surgical instrument and wherein the reservoir created by the pooled coating is configured to coat a second surgical instrument inserted into the wound site after the first surgical instrument is removed; and
 wherein the coating further comprises a binding substance that is configured to act as a sealant or adhesive within the wound site.

5. The surgical device of claim 4 wherein the anti-microbial coating is povidone-iodine.

6. The surgical device of claim 4 wherein the anti-microbial coating is adhered to the shaft using a viscoelastic substance.

7. The surgical device of claim 4 wherein the anti-microbial coating is adhered to the shaft using a hydrophilic coating.

8. The surgical device of claim 4, wherein an amount of the coating configured to slough off is set by controlling a consistency of the coating.

9. The surgical device of claim 4, wherein the coating comprises a substance that is configured to act as a sealant or adhesive within the wound site.

* * * * *